United States Patent
Demolliens

(10) Patent No.: US 11,015,866 B2
(45) Date of Patent: May 25, 2021

(54) PROCESS AND PLANT FOR THE COMBINATION PRODUCTION OF A MIXTURE OF HYDROGEN AND NITROGEN AND ALSO OF CARBON MONOXIDE BY CRYOGENIC DISTILLATION AND CRYOGENIC SCRUBBING

(71) Applicant: L'Air Liquide, Societe Anonyme pour l'Etude et l'Exploitation des Procedes Georges Claude, Paris (FR)

(72) Inventor: Bertrand Demolliens, Paris (FR)

(73) Assignee: L'Air Liquide, Societe Anonyme Pour l'Etude et l'Exploitation des Procedes Georges Claude, Paris (FR)

( * ) Notice: Subject to any disclaimer, the term of this patent is extended or adjusted under 35 U.S.C. 154(b) by 197 days.

(21) Appl. No.: 16/306,249

(22) PCT Filed: May 24, 2017

(86) PCT No.: PCT/FR2017/051281
§ 371 (c)(1),
(2) Date: Nov. 30, 2018

(87) PCT Pub. No.: WO2017/212136
PCT Pub. Date: Dec. 14, 2017

(65) Prior Publication Data
US 2019/0128601 A1 May 2, 2019

(30) Foreign Application Priority Data

Jun. 6, 2016 (FR) .................................... 1655118

(51) Int. Cl.
*F25J 3/02* (2006.01)
*C01B 3/02* (2006.01)
(Continued)

(52) U.S. Cl.
CPC .......... *F25J 3/0223* (2013.01); *B01D 53/002* (2013.01); *B01D 53/1406* (2013.01);
(Continued)

(58) Field of Classification Search
CPC ........ F25J 3/0271; F25J 3/0665; F25J 3/0675; F25J 3/0261; F25J 3/0223; F25J 2215/14;
(Continued)

(56) References Cited

U.S. PATENT DOCUMENTS

| | | | |
|---|---|---|---|
| 6,178,774 B1 * | 1/2001 | Billy | C01B 3/025 62/620 |
| 7,617,701 B2 * | 11/2009 | Billy | C01B 3/506 62/617 |
| 2011/0138853 A1 * | 6/2011 | Haik-Beraud | F25J 3/0233 62/617 |

FOREIGN PATENT DOCUMENTS

| | | |
|---|---|---|
| DE | 37 41 906 | 6/1989 |
| EP | 0 317 851 | 5/1989 |

(Continued)

OTHER PUBLICATIONS

International Search Report and Written Opinion for PCT/FR2017/051281, dated Aug. 8, 2017.
(Continued)

*Primary Examiner* — Brian M King
(74) *Attorney, Agent, or Firm* — Justin K. Murray

(57) ABSTRACT

Process for the combined production of a mixture of hydrogen and nitrogen, and of carbon monoxide by cryogenic distillation and cryogenic scrubbing, wherein a methane-rich liquid is introduced at a first intermediate level of a scrubbing column as first scrubbing liquid and at least one nitrogen-rich liquid is introduced at a level higher than the first level of the scrubbing column as second scrubbing
(Continued)

liquid and a mixture of hydrogen and nitrogen is drawn off as overhead gas from the scrubbing column.

16 Claims, 3 Drawing Sheets

(51) Int. Cl.
| | | |
|---|---|---|
| *C01B 3/50* | (2006.01) | |
| *C01B 3/52* | (2006.01) | |
| *C01B 32/40* | (2017.01) | |
| *B01D 53/00* | (2006.01) | |
| *B01D 53/14* | (2006.01) | |
| *B01D 53/18* | (2006.01) | |
| *C07C 7/04* | (2006.01) | |

(52) U.S. Cl.
CPC ..... *B01D 53/1418* (2013.01); *B01D 53/1493* (2013.01); *B01D 53/18* (2013.01); *C01B 3/025* (2013.01); *C01B 3/506* (2013.01); *C01B 3/52* (2013.01); *C01B 32/40* (2017.08); *C07C 7/04* (2013.01); *F25J 3/0233* (2013.01); *F25J 3/0252* (2013.01); *F25J 3/0261* (2013.01); *F25J 3/0276* (2013.01); *B01D 2252/10* (2013.01); *B01D 2252/205* (2013.01); *C01B 2203/046* (2013.01); *C01B 2203/047* (2013.01); *C01B 2203/048* (2013.01); *C01B 2203/0415* (2013.01); *C01B 2203/068* (2013.01); *C01B 2210/007* (2013.01); *C01B 2210/0025* (2013.01); *C01B 2210/0053* (2013.01); *F25J 2200/70* (2013.01); *F25J 2200/76* (2013.01); *F25J 2200/94* (2013.01); *F25J 2205/04* (2013.01); *F25J 2205/30* (2013.01); *F25J 2205/66* (2013.01); *F25J 2210/42* (2013.01); *F25J 2215/02* (2013.01); *F25J 2245/42* (2013.01); *F25J 2270/04* (2013.01); *F25J 2270/24* (2013.01)

(58) Field of Classification Search
CPC ........... F25J 2215/0266; F25J 2215/067; F25J 2210/80; F25J 2215/80; F25J 2220/80; B01D 53/1475; C01B 3/506
See application file for complete search history.

(56) References Cited

FOREIGN PATENT DOCUMENTS

| EP | 0 465 366 | 1/1992 |
|---|---|---|
| EP | 0 790 212 | 8/1997 |
| EP | 0 928 937 | 7/1999 |
| EP | 0 937 681 | 8/1999 |
| EP | 1 245 533 | 10/2002 |
| FR | 2 807 504 | 10/2001 |
| FR | 2 807 505 | 10/2001 |
| WO | WO 2008 087318 | 7/2008 |

OTHER PUBLICATIONS

McNeil, et al. "Process and Apparatus for Separation of Nitrogen from Carbon Monoxide," Research Disclosure, Mason Publications, Hampshire, GB, vol. 426, No. 54, Oct. 1, 1999, 3 pages.

* cited by examiner

PROCESS AND PLANT FOR THE COMBINATION PRODUCTION OF A MIXTURE OF HYDROGEN AND NITROGEN AND ALSO OF CARBON MONOXIDE BY CRYOGENIC DISTILLATION AND CRYOGENIC SCRUBBING

CROSS REFERENCE TO RELATED APPLICATIONS

This application is a § 371 of International PCT Application PCT/FR2017/051281, filed May 24, 2017, which claims the benefit of FR 1655118, filed Jun. 6, 2016, both of which are herein incorporated by reference in their entireties.

FIELD OF THE INVENTION

The present invention relates to a process and plant for the combined production of a mixture of hydrogen and nitrogen, optionally constituting an ammonia synthesis gas, and also of carbon monoxide and optionally of methane by cryogenic distillation and cryogenic scrubbing.

BACKGROUND OF THE INVENTION

It is known to use methane scrubbing type processes, described in EP 0 465 366, in order to separate a synthesis gas into its various constituents. This process is based in particular on the use of a fraction of a methane-rich fluid recovered at the bottom of a $CO/CH_4$ column as scrubbing fluid of the first two columns, the other fraction of this fluid then being recovered in the form of a methane purge.

By thermodynamic equilibrium between the scrubbing methane and the column overhead gas, a portion of the methane is then lost in the overhead gas of the two columns. The scrubbing of the stripping column in order to increase the yield is described in EP 0 317 851.

It will therefore be necessary to have, at any moment, a sufficient amount of methane in the gas to be treated in order to compensate for these methane losses. If the synthesis gas to be treated does not contain enough methane, it will not be possible to use this process as is. It will therefore be necessary to use a makeup of methane-rich gas in order to artificially increase the content of methane in the incoming gas to be treated in order to be able to carry out a methane scrubbing as described in DE 37 41 906 A1.

Using a partial condensation process considerably reduces the CO extraction yield compared to methane scrubbing. It is necessary in this case to consume more "fuel" upstream (natural gas, naphtha, coal, etc.) to produce the synthesis gas in order to obtain the same production of carbon monoxide.

It is also known to use to treat a hydrogen-rich gas with liquid nitrogen in a scrubbing column in order to create a gas mixture needed for the synthesis of ammonia, having a stoichiometry in the vicinity of $3H_2$ per $1N_2$.

Certain documents, such as EP 0 937 681 A1, already tackle the coproduction of CO and of gas for ammonia. Nevertheless, the main defect thereof is that of:
- either reducing the CO extraction yield (typically around 8-10% of CO is lost in the liquid purge in the middle of the scrubbing column)
- or contaminating the CO product with nitrogen (an additional column and energy are then needed to re-separate this mixture).

SUMMARY OF THE INVENTION

The objective of certain embodiments of the invention is to couple the production of carbon monoxide with that of a mixture for the production of ammonia. An additional section is added to the top of the scrubbing column in order to successively scrub the synthesis gas with (from top to bottom) nitrogen and methane. The added nitrogen will not be found in CO product. Nevertheless the nitrogen present in the synthesis gas at the inlet will be found at the outlet in the CO product, in the case where there is no nitrogen removal column. A stripping column could also be added which will make it possible to recover a portion of the methane that would otherwise have been lost with the scrubbing column overhead gas. This stripping column may be formed by a chamber with a single theoretical plate, for example a separator vessel or a chamber that enables a separation equivalent to several theoretical plates.

The additional recovery of this methane may make it possible:
to use a methane scrubbing process with small amounts of methane in the synthesis gas.
Typically, the synthesis gas produced by an ATR is quite lean in methane, being at around 1 mol %.
A methane content lower than 0.4 mol % in the synthesis gas at the inlet becomes sufficient for carrying out a methane scrubbing.
Otherwise
It would have been necessary either to perform a partial condensation process with a significant loss of CO yield
It would have been necessary to import an additional gas G1 in order to artificially increase the content of methane in the incoming gas to be treated in order to be able to carry out a methane scrubbing as described in DE 37 41 906 A1. Therefore more gas is treated for the same production of CO, which requires larger equipment and/or greater energy consumed: this may potentially import impurities present in the gas G1 and not in the synthesis gas that it will then be necessary to deal with.
It is also possible to carry out an internal recycling of methane as described in EP 0 790 212 A1 which also makes it possible to help
to recover more methane in order to then be able to produce it as liquid or gas.
Coupling these two processes also makes it possible to use only a single cold box instead of two cold boxes and also to reduce the size of the CO turbine relative to a conventional methane scrubbing and therefore to reduce the CO cycle flow (and therefore to consume less energy). Indeed, the mixing of nitrogen and hydrogen is endothermic, which makes it possible to create cold by a means other than the CO turbine.

According to one subject of the invention, a process is provided for the combined production of a mixture of hydrogen and nitrogen, of carbon monoxide and optionally of methane and optionally of nitrogen by cryogenic distillation and cryogenic scrubbing, wherein:
i) a gas mixture containing at least hydrogen, carbon monoxide and methane is cooled in a heat exchanger,
ii) the cooled mixture is sent to a scrubbing column,
iii) a methane-rich liquid is introduced at a first intermediate level of the scrubbing column as first scrubbing liquid,
iv) at least one nitrogen-rich liquid is introduced at a level higher than the first level of the scrubbing column as second scrubbing liquid, v) a mixture of hydrogen and nitrogen is drawn off as overhead gas from the scrubbing column, vi) a bottoms liquid is drawn off from the scrubbing column and sent to a stripping column, vii) a liquid is drawn off level with an intermediate section of the scrubbing column which is sent either to the heat exchanger, or to a stripping column overhead gas line, or to a second stripping column, viii) a bottoms liquid is drawn off from the stripping column and sent to a column for separating carbon monoxide and methane, ix) at least one portion of the bottoms liquid from the separating column constitutes the liquid of step iii), and x) a fluid rich in carbon monoxide is drawn off from the separating column.

According to other optional aspects of the invention:
- the process is kept cold at least partially by expansion of at least one portion of the fluid rich in carbon monoxide or of at least one portion of the overhead gas from the stripping column in a turbine,
- the process is kept cold at least partially by mixing the overhead gas from the scrubbing column with a nitrogen-rich liquid originating from an external source at an intermediate temperature of the heat exchanger and/or at the temperature of the cold end of the heat exchanger,
- the scrubbing column, the stripping column and the separating column are in the same insulated enclosure,
- the gas mixture contains at most 0.4 mol % of methane and constitutes the only source of methane for the process nor of internal recycling of methane,
- a portion of the bottoms liquid from the separating column is recovered as methane-rich product in liquid form or in gaseous form, after having vaporized it in the heat exchanger,
- the nitrogen-rich liquid from step iv) originates from an external source and is not contained in the gas mixture upstream of the heat exchanger,
- the nitrogen-rich liquid from step iv) does not originate from an external source and is contained in the gas mixture upstream of the heat exchanger,
- a first nitrogen-rich liquid from step iv) originates from an external source and is not contained in the gas mixture upstream of the heat exchanger and a second nitrogen-rich liquid from step iv) does not originate from an external source and is contained in the gas mixture upstream of the heat exchanger,
- the at least one nitrogen-rich liquid is sent to the top of the scrubbing column,
- a gas drawn off from an intermediate region of the scrubbing column is cooled with a liquid rich in carbon monoxide drawn off from the separating column and the cooled gas is sent back to the scrubbing column,
- the overhead gas from the scrubbing column contains at least five, or even at least nine parts of hydrogen per one part of nitrogen and optionally is enriched in nitrogen in order to reach three parts of hydrogen,
- the gas mixture contains nitrogen and at least one portion of the nitrogen-rich liquid sent to the scrubbing column originates from a nitrogen removal column which purifies the fluid rich in carbon monoxide of nitrogen,
- the methane-rich liquid produced contains at least one other heavier hydrocarbon, such as ethane.

According to another subject of the invention, a plant is provided for the combined production of a mixture of hydrogen and nitrogen, of carbon monoxide and of methane and optionally of nitrogen by cryogenic distillation and cryogenic scrubbing comprising a heat exchanger, a scrubbing column, a stripping column, a column for separating carbon monoxide and methane, a line for sending a gas mixture containing at least hydrogen, carbon monoxide and methane to be cooled, a line for sending the cooled mixture from the heat exchanger to the scrubbing column, a line for introducing a methane-rich liquid at a first intermediate level of the scrubbing column as first scrubbing liquid, at least one line for introducing a nitrogen-rich liquid at a level higher than the first level of the scrubbing column as second scrubbing liquid, a line for drawing off a mixture of hydrogen and nitrogen as overhead gas from the scrubbing column, a line for drawing off a bottoms liquid from the scrubbing column and for sending the bottoms liquid from the scrubbing column to the stripping column, a line for drawing off a liquid level with an intermediate section of the scrubbing column and for sending it either to the heat exchanger, or to a stripping column overhead gas line, or to a second stripping column, a line for drawing off a bottoms liquid from the stripping column and sending it to the column for separating carbon monoxide and methane, at least one portion of the bottoms liquid from the separating column constituting the methane-rich liquid and a line for drawing off a fluid rich in carbon monoxide from the separating column.

The principle of the invention is, starting from the methane scrubbing process, to add a section at the top of the scrubbing column. The first (bottom) section of the scrubbing column treats the synthesis gas with liquid methane in a conventional manner. The gas will then continue to the second section. Before integrating the second section, the gas could be cooled to −181° C. with liquid CO in order to recover methane which will be condensed (in an analogous manner to that described in FR 2 807 505). The scrubbing column bottoms liquid is conventionally sent to a stripping column then to the CO/CH$_4$ column.

In the second (top) section, the gas is scrubbed with nitrogen. The bottoms liquid from this second section will then be recovered and either vaporized directly (FIG. 1), or sent to a second stripping column (FIG. 2). This second stripping column will be operated at a pressure of 3 bar approximately. The bottom of this second stripping column will be reheated in order to reduce the nitrogen concentration of the liquid so as not to contaminate the CO product with nitrogen. The liquid from the bottom of this column will be sent to the CO/CH$_4$ column. A small fraction of CO (around 0.1% of the incoming CO flow) is recovered in passing which also makes it possible to increase the CO yield. The overhead gas from the second stripping column will be reheated in the main exchanger then purged.

The scrubbing column overhead gas that therefore no longer contains methane after the nitrogen scrubbing is either sent directly to the exchanger 7, or sent to a vaporizer-condenser in order to generate liquid CO from LP CO. (Specifically, N$_2$/H$_2$ mixing is endothermic and the temperature of this gas is −193° C. approximately.)

It will be possible to mix the nitrogen necessary for the adjustment of the H$_2$/N$_2$ ratio:

i) directly at low temperature (i.e. without reheating of the hydrogen-rich scrubbing column overhead gas in the exchanger, or at the cold end) and/or ii) at an intermediate level of the exchanger (i.e. after partial reheating of the scrubbing column overhead gas in the main exchanger).

These two solutions making it possible to produce cold and therefore to reduce the makeup of cold by the turbine.

It is also possible to carry out the mixing at high temperature, that is to say downstream of the main exchanger, which generally makes it possible to reduce the investment.

It will be possible to send this mixture of gases, in the same way as the top of the column, either directly to the exchanger 7, or sent to a vaporizer-condenser in order to generate liquid CO from LP CO, or used to cool the methane scrubbing column section in an analogous manner to FR 2 807 504.

It is also possible to add nitrogen partially at low temperature or at an intermediate level of the exchanger and carry out the final mixing in order to achieve the desired stoichiometry at high temperature. The invention will be described in greater detail by referring to the three figures that illustrate processes according to the invention.

BRIEF DESCRIPTION OF THE DRAWINGS

Further features, advantages and possible applications of the invention can also be taken from the following description of exemplary embodiments and numerical examples as well as the drawing. All features described and/or illustrated form the subject-matter of the invention per se or in any combination, independent of their inclusion in the claims or their back-reference.

DETAILED DESCRIPTION OF THE INVENTION

Figure 1:
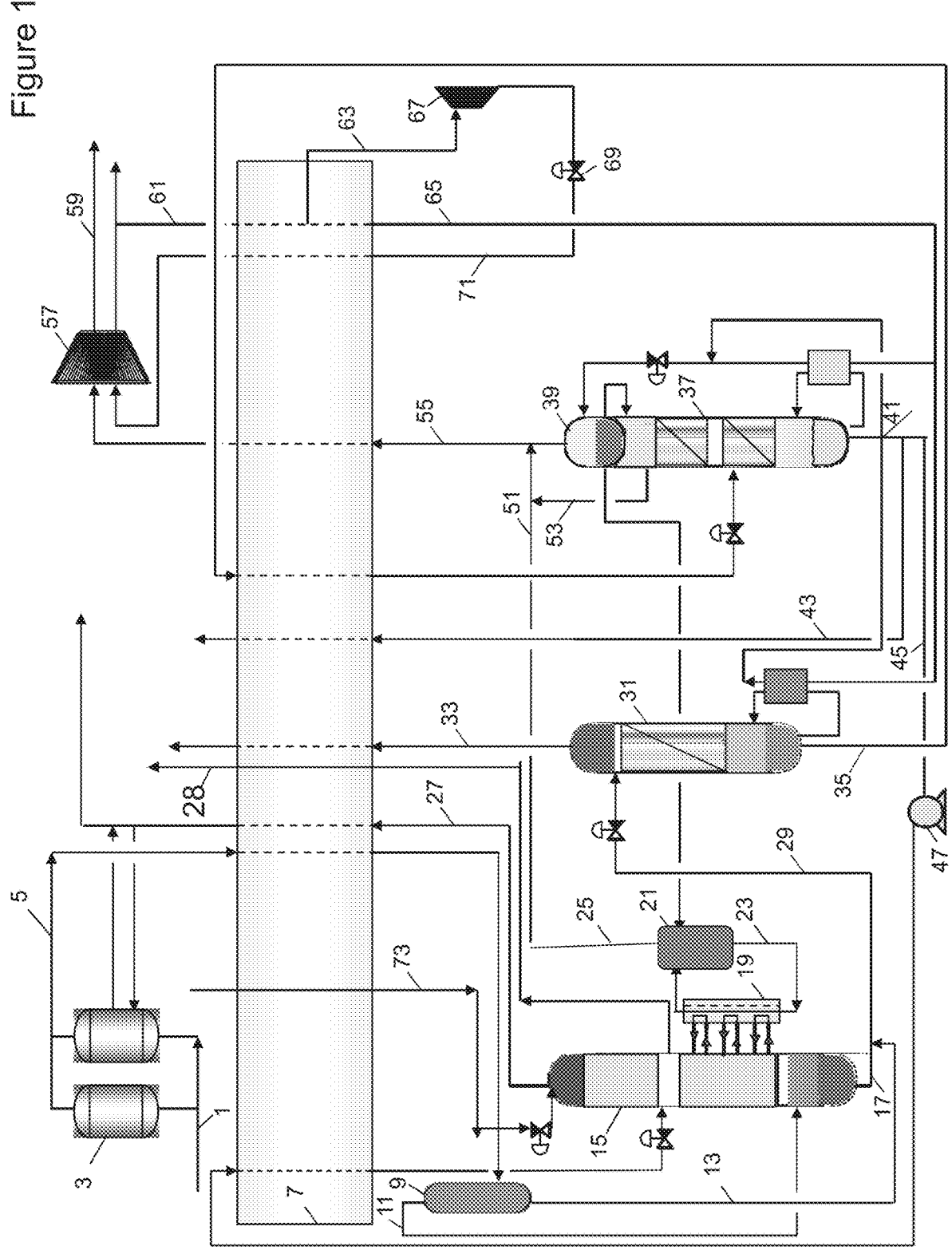
FIG. 1 provides a first embodiment of the present invention.

According to the process from FIG. 1, a flow of synthesis gas containing at least hydrogen, carbon monoxide and methane 1 is purified of water, carbon dioxide, methanol and other impurities in the purification unit 3 and then the flow 5 of dry synthesis gas is cooled in the heat exchanger 7, which is preferably a brazed aluminum plate exchanger. The cooled gas is sent to a phase separator 9 and the gas formed 11 is sent to the bottom of a scrubbing column 15. The scrubbing column is fed at an intermediate level, referred to as first intermediate level of the scrubbing column 15, with a methane-rich liquid 45 as first scrubbing liquid. A nitrogen-rich liquid 73 is introduced at a level higher than the first level of the scrubbing column 15 as second scrubbing liquid. A mixture of hydrogen and nitrogen 27 is drawn off as overhead gas from the scrubbing column 15 and a bottoms liquid is drawn off from the scrubbing column. The overhead gas 27 from the scrubbing column contains at least five, or even at least nine parts of hydrogen per one part of nitrogen and is enriched in nitrogen in order to reach three parts of hydrogen.

The bottoms liquid 17 from the scrubbing column is mixed with the liquid 13 from the phase separator 9 and the mixture 29 is sent to the top of a stripping column 31. An intermediate liquid 28 is drawn off at the first intermediate level of the scrubbing column 51 and sent to be vaporized in the heat exchanger 7. Without this drawing off, the product rich in carbon monoxide would be contaminated with nitrogen. A bottoms liquid 35 is drawn off from the stripping column 31 and sent to a column for separating carbon monoxide and methane 37 at an intermediate level after cooling in the heat exchanger 7. At least one portion 45 of the bottoms liquid 41 from the separating column 37 constitutes the first scrubbing liquid after pressurization in the pump 47. A fluid rich in carbon monoxide 53 is drawn off at the top of the separating column 37. The separating column 37 comprises a store of liquid carbon monoxide 39 at the top of the column. The gas 53 and the gas from the store are sent as gas 55 to a carbon monoxide compressor 57 in order to provide the product rich in carbon monoxide 59. A portion 61 of the carbon monoxide is cooled in the heat exchanger 7 and split into two; one portion 63 is expanded in a turbine 67 and a valve 69 in order to be reheated and sent back to the compressor 57. The remainder 65 is used to reboil the columns 31 and 37 and to feed the store 39.

Liquid carbon monoxide 49 from the store 39 is used to cool intermediate fluids of the scrubbing column at a point below the inlet of the first scrubbing liquid. The chamber 21 receives the liquid and liquid 23 is sent to an exchanger 19 in order to cool the intermediate flows. The gas 25 from the chamber is sent back to the compressor 57.

A flash gas 33 leaves the top of the stripping column 31 and a methane-rich product 43 is optionally drawn off from the CO/CH$_4$ column 37 in liquid form and vaporized in the exchanger 7.

Figure 2:
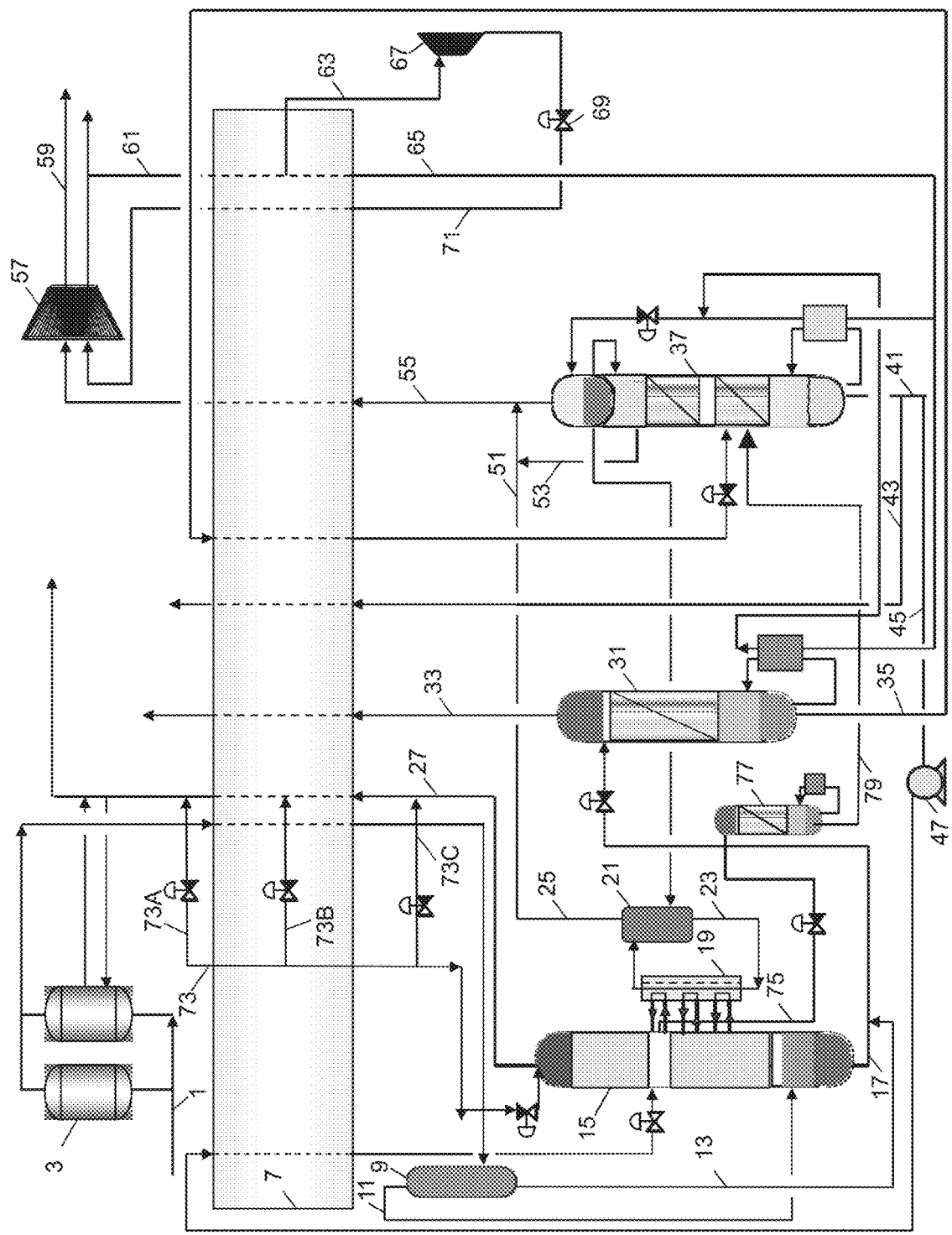
FIG. 2 provides a second embodiment of the present invention.

The process from FIG. 2 differs from that of FIG. 1 in that a second stripping column 77 has been added, operating at around 3 bar. Fed at the top by a liquid taken above the inlet of the first scrubbing liquid, it is heated by the carbon monoxide cycle. The bottoms liquid 79 is sent to the CO/CH$_4$ column 37 at the same level as the flow 35.

In order to arrive at the required ratio of hydrogen and nitrogen, it is possible to add nitrogen from the external source to the overhead gas from the scrubbing column upstream of the heat exchanger and/or at an intermediate level of the heat exchanger and/or downstream of the heat exchanger.

It will be understood in the examples from the two figures that the overhead gas from the scrubbing column may contain hydrogen and nitrogen in a 3:1 ratio as required for an ammonia or non-ammonia synthesis gas. In the case where the nitrogen present would be insufficient, nitrogen may be added at the outlet of the column as illustrated for FIG. 2 in order to achieve the required ratio.

Figure 3:
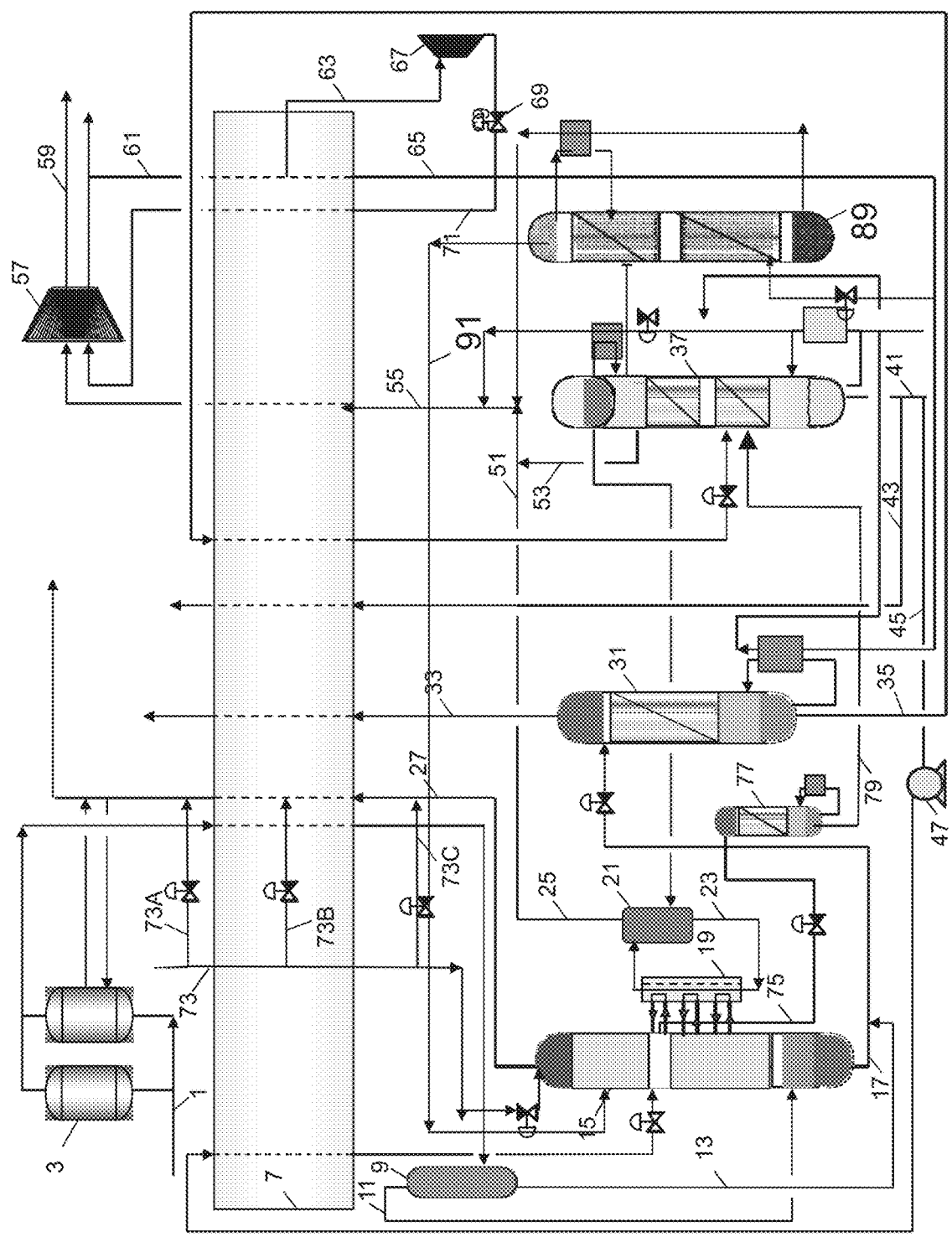
FIG. 3 provides a third embodiment of the present invention.

In FIG. 3, a nitrogen removal column 89 has been added. Fed at the bottom by carbon monoxide 65 originating from the compressor 57, it produces nitrogen-free carbon monoxide at the bottom which feeds the compressor 57. The nitrogen-rich flow produced at the top of the column 89 is expanded, liquefied and sent to the top of the column 15 as scrubbing liquid. In this case, the flow 73 may be reduced, or even no supply of nitrogen other than the feed gas 1 is needed. In the example, the liquid 91 is introduced into the column 15 below the inlet of the liquid 73.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

The invention claimed is:

1. A process for the combined production of a mixture of hydrogen and nitrogen, of carbon monoxide by cryogenic distillation and cryogenic scrubbing, wherein the process comprises the steps of:
   i) cooling, in a heat exchanger, a gas mixture containing at least hydrogen, carbon monoxide and methane;
   ii) sending the cooled mixture to a scrubbing column;
   iii) introducing a methane-rich liquid at a first intermediate level of the scrubbing column as a first scrubbing liquid;
   iv) introducing at least one nitrogen-rich liquid at a level higher than the first level of the scrubbing column as a second scrubbing liquid,;
   v) withdrawing a mixture of hydrogen and nitrogen as an overhead gas from the scrubbing column;
   vi) withdrawing a first bottoms liquid from the scrubbing column and then sending said first bottoms liquid to a stripping column;
   vii) withdrawing a liquid that is level with an intermediate section of the scrubbing column and sending said liquid either to the heat exchanger, or to a stripping column overhead gas line, or to a second stripping column;
   viii) withdrawing a second bottoms liquid from the stripping column and then sending to a column configured to separate carbon monoxide and methane; and
   ix) withdrawing a fluid rich in carbon monoxide from the separating column;
   x) withdrawing a third bottoms liquid from the separating column, wherein at least one portion of the third bottoms liquid from the separating column constitutes the methane-rich liquid of step iii).

2. The process as claimed in claim 1, wherein the process is kept cold at least partially by expansion of at least one portion of the fluid rich in carbon monoxide or of at least one portion of the overhead gas from the stripping column in a turbine.

3. The process as claimed in claim 1, wherein the process is kept cold at least partially by mixing the overhead gas from the scrubbing column with a nitrogen-rich liquid originating from an external source at an intermediate temperature of the heat exchanger and/or at the temperature of the cold and/or hot end of the heat exchanger.

4. The process as claimed in claim 1, wherein the process is kept cold at least partially by expansion of at least one portion of the fluid rich in carbon monoxide or of at least one portion of the overhead gas from the stripping column in a turbine, and wherein the process is kept cold at least partially by mixing the overhead gas from the scrubbing column with a nitrogen-rich liquid originating from an external source at an intermediate temperature of the heat exchanger and/or at the temperature of the cold and/or hot end of the heat exchanger.

5. The process as claimed in claim 1, wherein the scrubbing column, the stripping column and the separating column are in the same insulated enclosure.

6. The process as claimed in claim 1, wherein the gas mixture contains at most 0.4 mol% of methane and constitutes the only source of methane for the process.

7. The process as claimed in claim 1, wherein a second portion of the third bottoms liquid from the separating column is recovered as methane-rich product in liquid form or in gaseous form, after having vaporized the second portion of the third bottoms liquid in the heat exchanger.

8. The process as claimed in claim 1, wherein the nitrogen-rich liquid from step iv) originates from an external source and is not contained in the gas mixture upstream of the heat exchanger.

9. The process as claimed in claim 1, wherein the nitrogen-rich liquid is sent to the top of the scrubbing column.

10. The process as claimed in claim 1, wherein a gas drawn off from an intermediate region of the scrubbing column is cooled with a liquid rich in carbon monoxide drawn off from the separating column and the cooled gas is sent back to the scrubbing column.

11. The process as claimed in claim 1, wherein the overhead gas from the scrubbing column contains at least five parts of hydrogen per one part of nitrogen.

12. The process as claimed in claim 1, wherein the overhead gas from the scrubbing column contains at least nine parts of hydrogen per one part of nitrogen.

13. The process as claimed in claim 1, wherein the overhead gas from the scrubbing column is enriched in nitrogen such that the overhead gas contains three parts of hydrogen per one part of nitrogen.

14. A plant for the combined production of a mixture of hydrogen and nitrogen, of carbon monoxide by cryogenic distillation comprising:
   a heat exchanger;
   a scrubbing column;
   a stripping column;
   a column configured to separate carbon monoxide and methane;
   a first line for sending a gas mixture containing at least hydrogen, carbon monoxide and methane to be cooled;
   a second line for sending the cooled mixture from the heat exchanger to the scrubbing column;
   a third line for introducing a methane-rich liquid at a first intermediate level of the scrubbing column to act as a first scrubbing liquid;
   a fourth line for introducing a nitrogen-rich liquid at a level higher than the first level of the scrubbing column to act as a second scrubbing liquid;
   a fifth line for drawing off a mixture of hydrogen and nitrogen as overhead gas from the scrubbing column;
   a sixth line for drawing off a bottoms liquid from the scrubbing column and for sending the bottoms liquid from the scrubbing column to the stripping column;
   a seventh line for drawing off a liquid level with an intermediate section of the scrubbing column and for sending the liquid either to the heat exchanger, or to a stripping column overhead gas line, or to a second stripping column;

an eighth line for drawing off a bottoms liquid from the stripping column and sending the bottoms liquid from the stripping column to the column for separating carbon monoxide and methane, at least one portion of the bottoms liquid from the separating column constituting the methane-rich liquid; and a ninth line for drawing off a fluid rich in carbon monoxide from the separating column.

15. The plant as claimed in claim 14, wherein the seventh line is configured to send the liquid from the intermediate section of the scrubbing column to the second stripping column.

16. The process as claimed in claim 1, wherein the liquid that is withdrawn from the level that is at the intermediate section of the scrubbing column is sent to the second stripping column.

\* \* \* \* \*